US00RE38445E

(19) United States
(12) Reissued Patent
Pistl et al.

(10) Patent Number: US RE38,445 E
(45) Date of Reissued Patent: Feb. 24, 2004

(54) PISTOLS FOR SETTING SURGICAL CLAMPS

(75) Inventors: Gerald Pistl, Braunsdorf (DE); Petra Bohme, Chemnitz (DE)

(73) Assignee: Tyco Healthcare Group, LP, Norwalk, CT (US)

( * ) Notice: This patent issued on a continued prosecution application filed under 37 CFR 1.53(d), and is subject to the twenty year patent term provisions of 35 U.S.C. 154(a)(2).

(21) Appl. No.: 09/305,416

(22) Filed: May 5, 1999

Related U.S. Patent Documents

Reissue of:
(64) Patent No.: 5,626,586
Issued: May 6, 1997
Appl. No.: 08/410,172
Filed: Mar. 24, 1995

(30) Foreign Application Priority Data

May 5, 1994 (DE) ..... 44 15 891

(51) Int. Cl.[7] ..... A61B 17/00
(52) U.S. Cl. ..... 606/143; 606/142; 606/139; 227/901
(58) Field of Search ..... 606/143, 142, 606/139; 227/901

(56) References Cited

U.S. PATENT DOCUMENTS

| | | | |
|---|---|---|---|
| 4,491,133 | A | 1/1985 | Menges et al. |
| 5,104,395 | A | 4/1992 | Thornton et al. |
| 5,112,343 | A | 5/1992 | Thornton |
| 5,171,249 | A | 12/1992 | Stefanchik et al. |
| 5,246,450 | A | 9/1993 | Thornton et al. |
| 5,300,081 | A | 4/1994 | Young et al. |
| 5,383,881 | A | 1/1995 | Green et al. |
| 5,403,327 | A | 4/1995 | Thornton et al. |
| 5,474,566 | A | 12/1995 | Alesi et al. |

FOREIGN PATENT DOCUMENTS

| | | |
|---|---|---|
| DE | 4303544 A1 | 9/1993 |
| DE | 4415891.2 | 2/1995 |
| WO | WOA9314701 | 5/1993 |

*Primary Examiner*—Julian W. Woo

(57) ABSTRACT

A pistol for setting surgical clamps has a clamp magazine disposed at the distal end of a tubular endoscopic shaft, a feeding mechanism for the clamps, and forceps with an associated forceps closing mechanism for setting the clamps. The feeding mechanism and the forceps closing mechanism are operated using a hand grip of the pistol. The clamp magazine has a lower magazine part and an upper magazine part permanently disposed on the lower magazine part. The clamp magazine is insertable over guiding elements into the endoscopic shaft with the feeding mechanism and the clamps are contained in the clamp magazine. The forceps and the forceps closing mechanism are disposed below the clamp magazine with the forceps being exchangeable. The clamp magazine is open at an end facing the grip for introducing a push rod for a feeding slide with the feeding slide having a connecting piece into which the push rod is disposed and locked. An elastic latch locks the clamp magazine in the endoscopic shaft. The forceps closing mechanism has a leading incline engageable with a leading incline on the elastic latch to permit release of the elastic latch simultaneous with displacement of a filler piece on said forceps closing mechanism to permit release of the forceps.

16 Claims, 4 Drawing Sheets

PISTOLS FOR SETTING SURGICAL CLAMPS

Matter enclosed in heavy brackets [ ] appears in the original patent but forms no part of this reissue specification; matter printed in italics indicates the additions made by reissue.

BACKGROUND OF THE INVENTION

The present invention relates to a pistol for setting surgical clamps having a pistol grip for operating a forceps closing mechanism and a removable staple magazine.

For hygienic reasons, only disposable pistols are used at the present time for setting surgical clamps which results in high costs. From the German patent 4303544 A1, a reloading magazine is known, which is fastened to the distal end of an endoscopic shaft in order to transfer clamps from the reloading magazine into a magazine of the pistol. With the reloading magazine, the disposable pistol is kept in use during the period of the surgical intervention by the reloading of clamps. However it is a disadvantage that a complicated reloading mechanism is necessary that the reloading mechanism requires special dexterity for reloading and does not preclude mechanical malfunctions, such as jamming of the clamps during their transfer, as well as defects in the reloading magazine and in the forceps-closing device. Furthermore, the pistol is disposed of at the end of the surgical intervention because sterilization of the pistol is not practical since the pistol consists of several individual parts, which must be disinfected and cleaned individually. Additionally, special tools and knowledge are required for disassembling and assembling the pistol and there are individual parts, such as springs, which can be cleaned only with great difficulty.

SUMMARY OF THE INVENTION

Accordingly, it is an object of the invention to provide a pistol for setting surgical clamps which can be disassembled and assembled without mechanical aids and consists of a few, simple individual parts, which can easily be disinfected and cleaned, as well as sterilized in the assembled state.

Pursuant to the invention, a pistol for setting surgical clamps is provided comprising a clamp magazine disposed at the distal end of a tubular endoscopic shaft, a feeding mechanism for the clamps, and forceps with an associated forceps closing mechanism for setting the clamps. The feeding mechanism and the forceps closing mechanism are operated using a hand grip of the pistol. The clamp magazine has a lower magazine part and an upper magazine part permanently disposed on the lower magazine pan. The clamp magazine is insertable over guiding elements into the endoscopic shaft with the feeding mechanism and the clamps are contained in the clamp magazine. The forceps and the forceps closing mechanism are disposed below the clamp magazine with the forceps being exchangeable. The clamp magazine is open at an end facing the grip for introducing a push rod for a feeding slide with the feeding slide having a connecting piece into which the push rod is disposed and locked. An elastic latch locks the clamp magazine in the endoscopic shaft. The forceps closing mechanism has a leading incline engageable with a leading incline on the elastic latch to permit release of the elastic latch simultaneous with displacement of a filler piece on said forceps closing mechanism to permit release of the forceps.

A particular advantage of the invention lies in that the pistol, with the exception of the exchangeable clamp magazine, can be taken apart into a few individual parts in order to disinfect and clean the individual parts. It is very easy for medical personnel to prepare and sterilize the clamp pistol for an operation and to add a new and sterile clamp magazine. The costs associated with surgery and waste are largely decreased by this repeated use.

It is a further advantage of the present invention that the forceps locking mechanism and the clamp magazine locking mechanism can be operated simultaneously.

BRIEF DESCRIPTION OF THE DRAWINGS

The invention is described in greater detail in the following by means of an embodiment shown in the drawings, wherein.

DETAILED DESCRIPTION OF THE INVENTION

Figure 1:
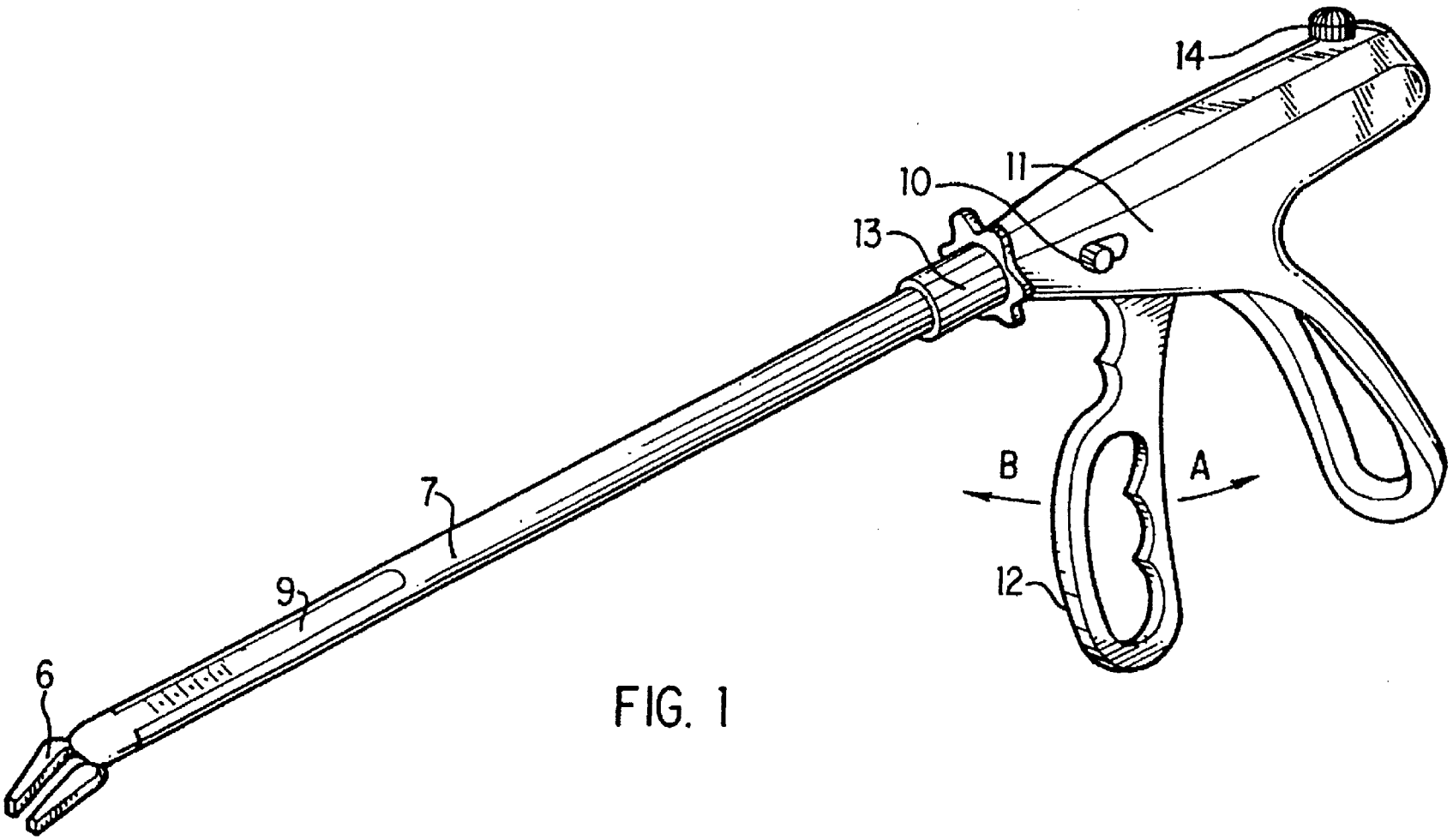
FIG. 1 shows an overall view of a pistol according to an embodiment of the present invention.

Referring to FIG. 1, a pistol for setting surgical clamps has a hand grip 11 and operating grip 12 connected to an endoscopic shaft 7, at the distal end of which a clamp magazine 9 and forceps 6 are disposed. When the operating grip 12 is moved in the direction A, the forceps 6 are closed and a clamp 3 is set. Depression of a knob 10 and movement of the operating grip 12 in direction B releases a forceps locking mechanism and clamp magazine locking mechanism to open them. The forceps 6 are adjustable circularly by means of locking-twisting adjustment 13 and the endoscopic shaft 7 is similarly detachable from the hand grip 11. The hand grip 11 is equipped with a rinsing connection 14 for disinfecting and cleaning.

Figure 2:
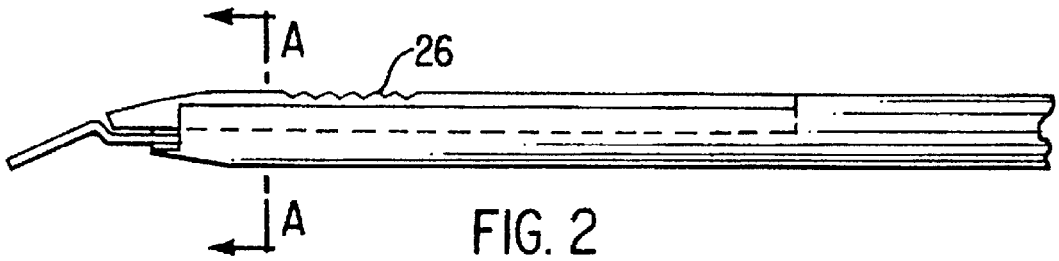
FIG. 2 shows a side view of an endoscopic shaft with a clamp magazine of the embodiment of FIG. 1.
Figure 3:
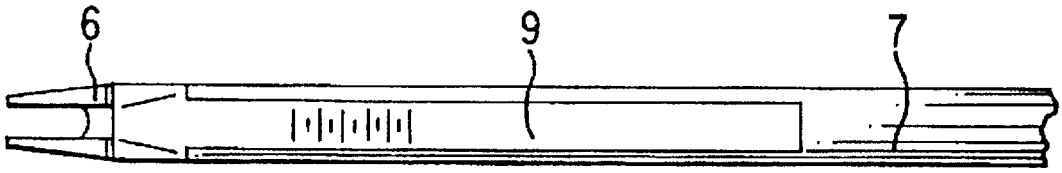
FIG. 3 shows a plan view of the endoscopic shaft with the clamp magazine of FIG. 2.

Referring to FIGS. 2 and 3, a front part of the endoscopic shaft 7 is shown with the clamp magazine 9 and forceps 6 installed. The clamp magazine has a grip element 26 on a top surface thereof to facilitate insertion and handling of the clamp magazine 9.

Figure 4:
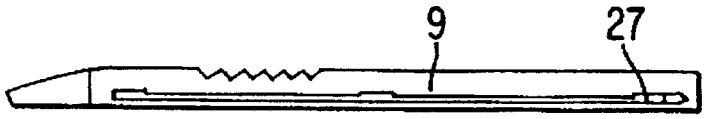
FIG. 4 shows a side view of the clamp magazine of FIG. 2.
Figure 5:
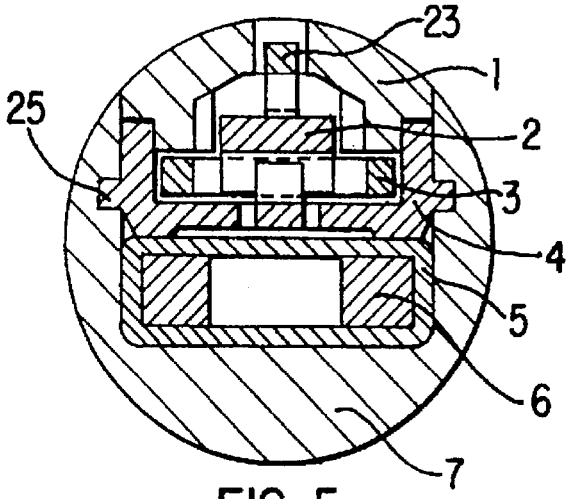
FIG. 5 shows a transverse section through A—A of FIG. 2.

Referring to FIGS. 4 and 5, the clamp magazine 9 is shown as a component part and also in cross section inserted in the endoscopic shaft 7. The clamp magazine 9 has a slide member 27 which is an offset in the width of a lower magazine part 4 of the clamp magazine 9. The clamp magazine 9 is guided by the slide member 27 engaging two grooves 25 in the endoscopic shaft 7. The clamp magazine 9 includes an upper magazine part 1 connected permanently to the lower magazine part 4.

Figure 6:
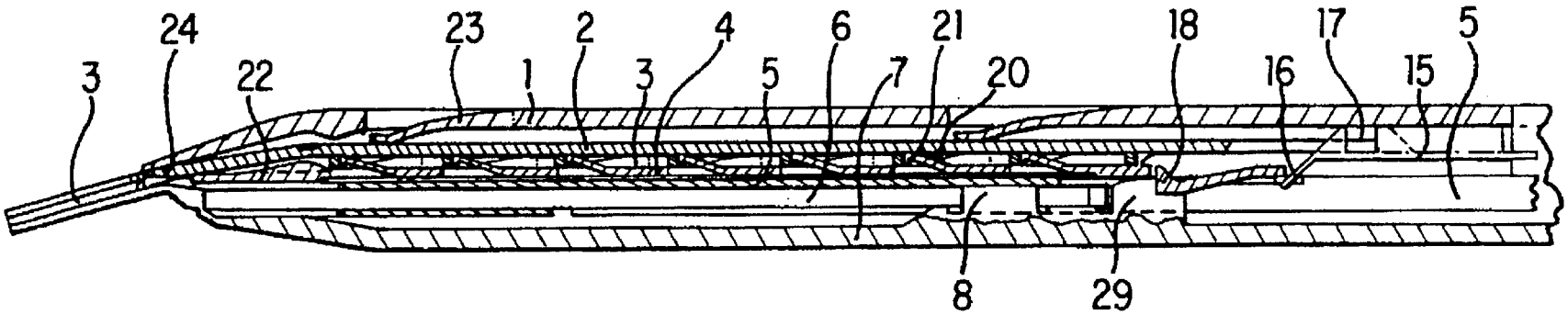
FIG. 6 shows a longitudinal section of the endoscopic shaft with the clamp magazine of FIG. 2.

Referring to FIGS. 5 and 6, a feeding slide 2 is provided for advancing clamps 3 and a spring catch 23 is biased against the feeding slide 2. The forceps 6 and a forceps closing device 5 are inserted below the clamp magazine 9. The clamp magazine 9 has an elastic latch 18 extending from a bottom thereof to secure the clamp magazine in the shaft 7 by engaging a catch member 29 of the endoscopic shaft 7.

A push rod 15 is over a leaf spring, which is not shown, and is thereby biased up to a stop. When the clamp magazine 9 is pushed into the endoscopic shaft 7, a connecting piece 17 extending from the feeding slide 2 is pushed upward over a leading incline 16 of the push rod 15 until it locks in place, the push rod 15 simultaneously being depressed downward against the bias of the leaf spring. The lift of the connecting piece 17 is limited in the axial direction by stops, which are not shown. Accordingly, the clamp magazine 9 is thus inserted in an operative state in the endoscopic shaft 7. The clamps 3 are transported and fed by way of cooperative motions of the feeding slide 2 and its latches 20 and spring catches 21 protruding from the lower magazine part 4. Each individual clamp 3 in the clamp magazine 9 is prevented by the spring catches 21 from moving in a direction away from the patient, that is, back into the endoscopic shaft 7 and away from the forceps 6. The accidental movement of the clamps 3 from the clamp magazine 9 in the direction of the patient is prevented by a guiding link 22 and, in addition, locking off the clamp pistol is realized by locking a slide catch 24 in the guiding link 22 when the clamp magazine 9 is empty.

To load the forceps 6 with a clamp 3, the feeding slide 2 is moved in a direction away from the patient by a distance a little less than twice the clamp spacing in the clamp magazine 9. The feeding slide 2 is lifted by the leading inclines at the latches 20 against the spring catches 23 and locks once again remote from the patient behind all clamps 3. Finally, the slide catch 24 locks behind the clamp 3 closest to the patient. The distance between two clamps 3 closest the patient is enlarged by a movement of the feeding slide in the direction of the patient. The foremost clamp 3 is pushed into the forceps 6. All other clamps 3 are transported in the direction of the patient by one spacing in the clamp magazine 9.

Figure 7:
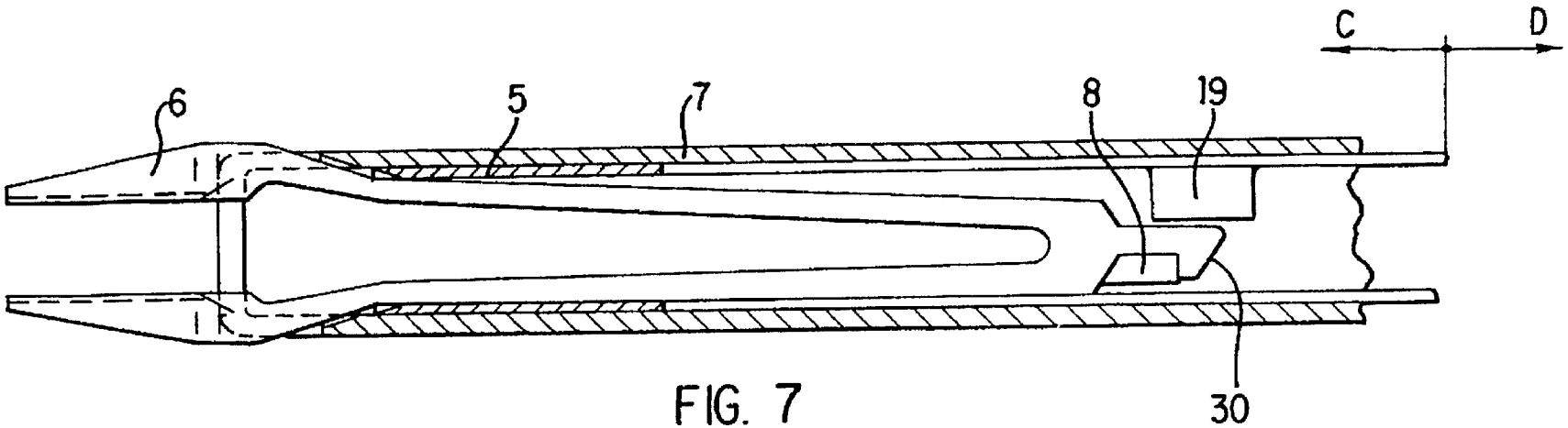
FIG. 7 shows details of a forceps closing device.

FIG. 7 illustrates the simple construction of the forceps 6 and the forceps closing mechanism 5. The forceps 6 are locked in place by a forceps locking mechanism including a catch 30 engaging a stop 8, extending from the inner bottom of the endoscopic shaft 7 as shown in FIG. 6, with the catch 30 being held in an engagement position with the stop 8 by a filler piece 19 on the forceps closing mechanism 5. When the forceps closing mechanism 5 is moved from the basic position in the direction C, the forceps 6 are closed. Moving the forceps closing mechanism from the basic position in the direction D opens the forceps locking mechanism by movement of the filler piece 19. At the same time, with the movement of the forceps closing mechanism 5 in the direction D, the elastic latch 18 is raised by sliding engagement of leading inclines on the forceps closing mechanism 5 and on the elastic latch 18, with respect to the relative motion of the forceps closing mechanism 5 and the elastic latch 18, and the clamp magazine 9 is unlocked accordingly.

What is claimed is:

[1. A clamping apparatus for applying surgical clamps, comprising:

a pistol grip actuator having an operating grip movable from an intermediate position in a first direction for setting one of said surgical clamps and in a second direction for disassembly of said clamping apparatus;

a hollow shaft having a first end removably connected to said pistol grip actuator;

a removable magazine for holding said surgical clamps;

slide means for slidably receiving said removable magazine in said hollow shaft through an open second end of said hollow shaft;

said removable magazine having a channel containing said surgical clamps;

a forceps closing member slidably disposed in said hollow shaft beneath said removable magazine and responsive to movement of said operating grip;

said removable magazine having an elastic catch biased downward for engaging a catch member of said hollow shaft extending through said forceps closing member;

forceps means, slidably disposed in said forceps closing member, for receiving and compressing one of said surgical clamps by a cam action movement of said forceps closing member in response to actuation of said operating grip in said first direction;

said forceps means having a catch hook engageable with a stop member extending from said hollow shaft and through said forceps closing means to maintain said forceps means fixed relative to said hollow shaft permitting said cam action movement of said forceps closing means to compress said one of said surgical clamps;

said forceps closing means having a filler member disposed to maintain engagement of said catch hook with said stop member during said cam action movement of said forceps closing means;

said magazine having a feeding slide for advancing said surgical clamps toward said second end of said hollow shaft;

a push rod means extending from said pistol grip actuator into said hollow shaft responsive to movement of said operating grip in said first direction;

means for disengagably connecting said feeding slide with said push rod means to permit advancement of said surgical clamps in response to movement of said operating grip; and said forceps closing means being responsive to movement of said operating grip in said second direction to effect displacement of said filler member from said catch hook to permit removal of said forceps means and displacement of said elastic latch from said catch member to allow removal of said magazine.]

*2. A clamping apparatus for applying surgical clamps, comprising:*

*a pistol grip actuator having an operating grip moveable from an intermediate position in a first direction for setting a surgical clamp;*

*a hollow shaft with a first end connected to said pistol grip actuator and having guiding elements and a catch member;*

*a magazine having a channel for containing surgical clamps and slidably received within said hollow shaft by said guiding elements through an open second end of said hollow shaft, said magazine having a feeding slide for advancing said surgical clamps toward said second end of said hollow shaft;*

*an elastic latch extending from said magazine and engaging said catch member for securing said magazine within said hollow shaft;*

*a forceps closing member slidably disposed within said hollow shaft and responsive to movement of said operating grip;*

*a push rod extending from said pistol grip actuator and received by said hollow shaft, said rod responsive to movement of said operating grip in said first direction and in operative connection with said feeding slide and said forceps closing member, and*

*a forceps means, slidably disposed in said forceps closing member for receiving and compressing one of said*

*surgical clamps exterior of said hollow shaft by a cam action movement of said forceps closing member within said hollow shaft in response to actuation of said operating grip in said first direction.*

*3. The clamping apparatus of claim 2 wherein said pistol grip actuator is movable from an intermediate position in a second direction for disassembly of said clamping apparatus.*

*4. The clamping apparatus of claim 2 wherein said forceps means further comprises forceps, said forceps being removable.*

*5. The clamping apparatus of claim 2 wherein said hollow shaft is removable.*

*6. The clamping apparatus of claim 2 wherein said magazine is removable.*

*7. The clamping apparatus of claim 4 wherein said forceps further comprise a catch hook engageable with a stop member extending from said hollow shaft, said forceps means further comprising a filler member disposed to maintain engagement of said catch hook with said stop member, said stop member maintaining said forceps means fixed relative to said hollow shaft during cam action movement of said forceps closing member.*

*8. The clamping apparatus of claim 7 wherein said forceps closing means is responsive to movement of said operating grip from an intermediate position in a second direction to effect displacement of said filler member relative to said catch hook to permit removal of said forceps and displacement of said elastic latch from said catch member to allow removal of said magazine.*

*9. The clamping apparatus of claim 8 further comprising a knob member attached to said pistol grip whereby depression of said knob allows movement of said operating grip in a second direction.*

*10. The clamping apparatus of claim 4 whereby said forceps are rotatably adjustable by a twisting member of said first end of said hollow shaft.*

*11. The clamping apparatus of claim 2 wherein said pistol grip is equipped with a rinsing connection for disinfection and cleaning.*

*12. The clamping apparatus of claim 6 whereby said magazine is equipped with a grip element at its surface to facilitate handling and replacement of said magazine.*

*13. The clamping apparatus of claim 2 wherein said magazine further comprises spring catches to prevent clamp movement in a direction toward said first end.*

*14. The clamping apparatus of claim 2 wherein said magazine further comprises a guiding link to avoid undesired clamp movement in a direction toward said second end.*

*15. A clamping apparatus for applying surgical clamps, comprising:*

*a pistol grip actuator having an operating grip movable from an intermediate position in a first direction for setting one of said surgical clamps and in a second direction for disassembly of said clamping apparatus;*

*a hollow shaft having a first end removably connected to said pistol grip actuator;*

*a removable magazine having a channel for containing said surgical clamps;*

*a forceps closing member slidably disposed in said hollow shaft beneath said removable magazine and responsive to movement of said operating grip;*

*said magazine operatively engaging said hollow shaft;*

*forceps means, slidably disposed in said forceps closing member, for receiving and compressing one of said surgical clamps by a cam action movement of said forceps closing member in response to actuation of said operating grip in said first direction;*

*said forceps means having a catch hook engageable with a stop member extending from said hollow shaft and through said forceps closing means to maintain said forceps means fixed relative to said hollow shaft permitting said cam action movement of said forceps closing means to compress said one of said surgical clamps;*

*said forceps closing means having a filler member disposed to maintain engagement of said catch hook with said stop member during said cam action movement of said forceps closing means;*

*said magazine having a feeding slide for advancing said surgical clamps toward said second end of said hollow shaft;*

*a push rod means extending from said pistol grip actuator into said hollow shaft responsive to movement of said operating grip in said first direction;*

*means for disengagably connecting said feeding slide with said push rod means to permit advancement of said surgical clamps in response to movement of said operating grip; and*

*said forceps closing means being responsive to movement of said operating grip in said second direction to effect displacement of said filler member from said catch hook to permit removal of said forceps means and to effect disengagement of said magazine from said hollow shaft.*

*16. The clamping apparatus according to claim 15, wherein said hollow shaft includes a catch member and wherein said magazine includes an elastic latch biased downward for engaging said catch member of said hollow shaft.*

*17. The clamping apparatus according to claim 16, wherein said forceps closing means is responsive to a movement of said operating grip in said second direction to effect a displacement of said elastic latch from said catch member to allow for removal of said magazine from said hollow shaft.*

* * * * *